(12) United States Patent
L'Alloret

(10) Patent No.: US 7,883,692 B2
(45) Date of Patent: *Feb. 8, 2011

(54) POLYMER COMPRISING WATER SOLUBLE UNITS AND LCST UNITS, AND AQUEOUS COMPOSITION COMPRISING SAME

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/756,331

(22) Filed: Apr. 8, 2010

(65) Prior Publication Data

US 2010/0190870 A1 Jul. 29, 2010

Related U.S. Application Data

(60) Division of application No. 11/324,279, filed on Jan. 4, 2006, now Pat. No. 7,722,859, which is a continuation of application No. 10/312,592, filed as application No. PCT/FR01/02094 on Jun. 29, 2001, now Pat. No. 7,115,255.

(30) Foreign Application Priority Data

Jul. 21, 2000 (FR) ................................ 00 09614

(51) Int. Cl.
 A61Q 19/00 (2006.01)
 A61K 47/30 (2006.01)
 A61K 8/00 (2006.01)
 C08L 53/00 (2006.01)
 C08L 33/02 (2006.01)

(52) U.S. Cl. ................ 424/78.02; 524/1; 525/403; 525/404

(58) Field of Classification Search ............... None
See application file for complete search history.

(56) References Cited

U.S. PATENT DOCUMENTS

| | | | |
|---|---|---|---|
| 4,274,977 A | 6/1981 | Koerner et al. | |
| 4,559,226 A | 12/1985 | Fogel et al. | |
| 4,737,265 A | 4/1988 | Merchant et al. | |
| 4,839,167 A | 6/1989 | Yamamoto et al. | |
| 5,338,352 A | 8/1994 | Breneman et al. | |
| 5,509,913 A | 4/1996 | Yeo | |
| 5,730,966 A | 3/1998 | Torgerson et al. | |
| 5,939,485 A | 8/1999 | Bromberg et al. | |
| 6,001,367 A | 12/1999 | Bazin et al. | |
| 6,139,623 A | 10/2000 | Darwin et al. | |
| 6,159,457 A | 12/2000 | Mougin | |
| 6,280,755 B1 | 8/2001 | Berger et al. | |
| 6,284,233 B1 | 9/2001 | Simon et al. | |
| 6,284,281 B1 | 9/2001 | Chevalier et al. | |
| 6,413,526 B1 | 7/2002 | Bazin et al. | |
| 6,464,967 B1 | 10/2002 | Collin | |
| 6,486,213 B1 | 11/2002 | Chen et al. | |
| 6,689,856 B2 | 2/2004 | L'Alloret | |
| 6,692,733 B1 | 2/2004 | Mougin | |
| 6,878,754 B2 | 4/2005 | L'Alloret | |
| 6,998,426 B2 | 2/2006 | L'Alloret et al. | |
| 7,652,100 B2 * | 1/2010 | L'Alloret | 524/800 |
| 7,655,702 B2 * | 2/2010 | L'Alloret | 514/772.1 |
| 2002/0187173 A1 | 12/2002 | L'Alloret et al. | |
| 2002/0197231 A1 | 12/2002 | L'Alloret et al. | |
| 2003/0004258 A1 | 1/2003 | L'Alloret | |
| 2003/0031643 A1 | 2/2003 | L'Alloret et al. | |
| 2003/0059392 A1 | 3/2003 | L'Alloret | |
| 2003/0147832 A1 | 8/2003 | L'Alloret | |
| 2003/0158330 A1 | 8/2003 | L'Alloret | |
| 2004/0044130 A1 | 3/2004 | Labeau et al. | |
| 2005/0249683 A1 | 11/2005 | L'Alloret | |
| 2006/0111518 A1 * | 5/2006 | L'Alloret | 525/404 |

FOREIGN PATENT DOCUMENTS

| | | |
|---|---|---|
| EP | 0 583 814 | 2/1994 |
| EP | 0 629 649 | 12/1994 |
| EP | 0 722 994 | 7/1996 |
| EP | 0 754 446 | 1/1997 |
| EP | 0 858 795 | 8/1998 |
| EP | 0 987 016 | 3/2000 |
| EP | 0 998 905 | 5/2000 |
| EP | 1 043 345 | 10/2000 |
| EP | 1 046 388 | 10/2000 |
| EP | 1 055 694 | 11/2000 |
| JP | 61-245835 | 11/1986 |

(Continued)

OTHER PUBLICATIONS

F.E. Bailey, Jr., et al.: "Some properties of poly(ethylene oxide) in aqueous solution" *Journal of Applied Polymer Science*, vol. 1, No. 1, pp. 56-62 (1959).

(Continued)

*Primary Examiner*—Michael J Feely
(74) *Attorney, Agent, or Firm*—Oblon, Spivak, McClelland, Maier & Neustadt, L.L.P.

(57) ABSTRACT

The invention concerns a polymer comprising water soluble units and LCST units consisting of ethylene oxide and propylene oxide random copolymers, or one of its salts. The invention also concerns an aqueous composition in particular thickened, even gelled, comprising such a polymer or one of its salts and an aqueous phase.

20 Claims, No Drawings

FOREIGN PATENT DOCUMENTS

| | | |
|---|---|---|
| JP | 2-295912 | 12/1990 |
| JP | 9-227329 | 9/1997 |
| WO | WO 95/24430 | 9/1995 |
| WO | WO 97/00275 | 1/1997 |
| WO | WO 97 35814 | 10/1997 |
| WO | WO 98/29091 | 7/1998 |
| WO | WO 98/29092 | 7/1998 |
| WO | WO 98/29487 | 7/1998 |
| WO | WO 98 31643 | 7/1998 |
| WO | WO 98/48768 | 11/1998 |
| WO | WO 98/50005 | 11/1998 |
| WO | WO 99/27924 | 6/1999 |
| WO | WO 00/35961 | 6/2000 |

OTHER PUBLICATIONS

A. Durand, et al.: "Synthesis and thermoassociative properties in aqueous solution of graft copolymers containing poly(N-isopropylacrylamide) side chains" *Polymer*, vol. 40, No. 17, pp. 4941-4951 (1999).

M. Heskins, et al.: "Solution properties of Poly(N-isopropylacrylamide)" *J. Macromol.Sci. Chem.*, vol. A2 No. 8, pp. 1441-1455 Dec. 1968.

D. Hourdet, et al.: "Reversible thermothickening of aqueous polymer solutions" *Polymer*, vol. 35, No. 12, pp. 2624-2630 (1994).

D. Hourdet, et al.: "Synthesis of the thermoassociative copolymers" *Polymer*, vol. 38 No. 10, pp. 2535-2547 (1997).

F. L'Alloret, et al.: "Aqueous solution behavior of new thermoassociative polymers" *Colloid & Polymer Science*, vol. 273, No. 12, pp. 1163-1173 (1995).

F. L'Alloret, et al.: "Reversible thermoassociation of water-soluble polymers" *Revue De L'Institut Francais*, vol. 52 No. 2, pp. 117-128 (1997).

Lloyd D. Taylor, et al.: "Preparation of films exhibiting a balanced temperature dependence to permeation by aqueous solutions—a study of lower consolute behavior" *Journal of Polymer Science*, vol. 13, pp. 2551-2570 (1975).

* cited by examiner

US 7,883,692 B2

POLYMER COMPRISING WATER SOLUBLE UNITS AND LCST UNITS, AND AQUEOUS COMPOSITION COMPRISING SAME

CROSS-REFERENCE TO RELATED APPLICATIONS

This application is a division of U.S. application Ser. No. 11/324,279, filed Jan. 4, 2006, now U.S. Pat. No. 7,722,859, which is a continuation application of U.S. application Ser. No. 10/312,592, filed Aug. 11, 2003, now U.S. Pat. No. 7,115,255, which is a National Stage of PCT/FR01/02094, filed Jun. 29, 2001. This application also claims priority to French patent application 00/09614 filed Jul. 21, 2000, the entire contents of which are incorporated herein by reference.

FIELD OF THE INVENTION

The present invention relates to a novel family of polymers and their salts, which may be used in cosmetic or pharmacological compositions, especially to modify their rheological properties.

BACKGROUND OF THE INVENTION

The thickeners usually used in cosmetics or pharmaceuticals to control the rheology of compositions, especially aqueous compositions, generally undergo a reduction in viscosity when the temperature of the medium increases.

However, this behavior can present certain drawbacks, such as the change in the rheology of the composition as a function of changes in temperature (compositions which become fluid in summer and are more viscous in winter).

Particular polymers whose solubility in water is modified above a certain temperature are known in the prior art. These are polymers with a heat-induced demixing temperature (or cloud point) thus defining their region of water solubility. The minimum demixing temperature obtained as a function of the polymer concentration is known as the "LCST" (Lower Critical Solution Temperature).

Some of these polymers are especially described in the articles by Taylor et al., Journal of Polymer Science, part A; Polymer Chemistry, 1975, 13, 2551; by Bailey et al., Journal of Applied Polymer Science, 1959, 1, 56; and by Heskins et al., Journal of Macromolecular Science, Chemistry A2, 1968, 1441.

According to the teaching of patent applications EP-A-0583814 and EP-A-0629649, certain polymers having a critical temperature of the LCST type are used as thermoreversible viscosity-promoting additives in the manufacture of fluids or lubricants used in numerous industrial sectors.

Moreover, it is known, especially from patent application WO-95/24430, to use such heat-sensitive and pH-sensitive polymers in cosmetics or pharmaceuticals. The polymers described in said patent application may be of any chemical nature; in particular, they may be in the form of grafted copolymers comprising a pH-sensitive backbone with heat-sensitive grafts; or, conversely, in the form of a heat-sensitive backbone bearing pH-sensitive grafts; or alternatively in the form of block copolymers formed from pH-sensitive units and heat-sensitive units.

The heat-sensitive grafts or blocks therefore possess an LCST-type temperature as defined above. These blocks or grafts may be prepared by polymerization of vinyl monomers or by polymerization of cyclic ether monomers. In particular, these grafts or blocks may be in the form of poly(substituted N-alkyl)acrylamides or of block copolymers of ethylene oxide and of propylene oxide.

However, the heat-induced gelling properties of these polymers lead to opaque gels, as is pointed out in the description of said patent application. Now, this opacification of the aqueous solutions may be an unacceptable drawback for uses in cosmetics.

This is likewise the case with respect to patent application WO-97/00275, which describes in many cosmetic applications the use of polymers with heat-sensitive units, that are only in the form of block copolymers of ethylene oxide and of propylene oxide. Moreover, in said patent application, it is not easy to control the structure and the chemical nature of the synthesized polymers.

SUMMARY OF THE INVENTION

The aim of the present invention is to overcome the drawbacks of the prior art and to propose a novel family of polymers for controlling the rheology of aqueous compositions as a function of the temperature, while at the same time maintaining a certain level of transparency for the compositions.

Moreover, the chemical structure of this novel family of polymers makes it possible firstly to prepare them on demand, irrespective of the nature of the polymer backbone and/or of the grafts, and/or their respective amount and/or the desired structure (for example linear or branched); this especially makes it possible to adapt the desired properties, as a function of the intended applications.

One subject of the present invention is a polymer comprising water-soluble units bearing at least two reactive sites, and units having a temperature of LCST type bearing at least one reactive site, capable of reacting with the reactive sites borne by the water-soluble unit, so as to form a covalent bond, said units with an LCST consisting of random copolymers of ethylene oxide and propylene oxide, having an ethylene oxide number between 0 and 40 inclusive and a propylene oxide number between 15 and 60 inclusive, and the salts of this polymer.

Another subject of the invention is a thickened, or even gelled, aqueous composition comprising at least one polymer as defined above or one of its salts, and an aqueous phase.

DETAILED DESCRIPTION OF THE INVENTION

The salts of the polymers according to the invention may be of any type, organic or inorganic, for example sodium, magnesium, ammonium or triethanolamine salts.

Water-soluble polymers are thus obtained, especially having a solubility in water, at 20° C., of at least 10 g/l and preferably of at least 20 g/l. These water-soluble polymers make it possible to control the rheology of aqueous compositions as a function of the temperature, while at the same time maintaining the transparency of said compositions.

Moreover, it is possible to adjust as desired the relevant temperature range to the intended cosmetic application, by appropriately selecting the chemical nature of the water-soluble units, of the units with an LCST, and also the respective amounts thereof.

The polymers according to the present invention may be block polymers or grafted polymers, which comprise, on the one hand, water-soluble units, and on the other hand, units having a temperature of LCST type as defined below.

The polymers used in the context of the invention may thus be block polymers comprising, for example, water-soluble blocks alternating with blocks with an LCST.

These polymers may also be in the form of grafted polymers whose backbone is formed from water-soluble units, bearing grafts with an LCST. This structure may be partially crosslinked.

The expression "water-soluble units" means units that are soluble in water, at 20° C., to a proportion of at least 10 g/l and preferably of at least 20 g/l.

However, water-soluble units that may also be used include units not necessarily having the solubility mentioned above, but which, in solution at 1% by weight in water at 20° C., allow the production of a solution that is macroscopically homogeneous and transparent, that is to say having a maximum light transmittance value, irrespective of the wavelength of between 400 and 800 nm, through a sample 1 cm thick, of at least 80% and preferably of at least 85%.

The water-soluble units may be in the form of blocks within a block polymer, or may constitute the backbone of a grafted polymer.

These water-soluble units do not have a heat-induced demixing temperature of LCST type.

These water-soluble units may be obtained by free-radical polymerization of vinyl monomers, or by polycondensation, or alternatively may consist of existing natural polymers or modified natural polymers.

In all cases, the water-soluble units used bear at least two reactive sites.

Examples which may be mentioned include the monomers A listed below, which may be used to form said water-soluble units, alone or as a mixture as they are or in the form of organic or inorganic salts, for example, in the form of sodium, magnesium, ammonium or triethanolamine salts:

(meth)acrylic acid,
vinyl monomers of formula (IIa) below:

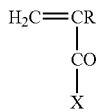

(IIa)

in which:
R is chosen from H, —$CH_3$, —$C_2H_5$ or —$C_3H_7$;
X is chosen from:
  alkyl oxides of —OR' type in which R' is a linear or branched, saturated or unsaturated hydrocarbon-based radical containing from 1 to 8 carbons, substituted with at least one hydroxyl (—OH); primary amine (—$NH_2$); secondary amine (—$NHR_1$) or tertiary amine (—$NR_1R_2$) group, with $R_1$ and $R_2$, independently of each other, representing a linear or branched, saturated or unsaturated hydrocarbon-based radical containing 1 to 25 carbon atoms, with the proviso that the sum of the carbon atoms of $R_1+R_2$ does not exceed 26; a halogen atom (iodine, bromine, chlorine or fluorine);
  groups —$NH_2$, —NHR' and —NR'R" in which R' and R" are, independently of each other, linear or branched, saturated or unsaturated hydrocarbon-based radicals containing 1 to 25 carbon atoms, with the proviso that the total number of carbon atoms of R'+R" does not exceed 26, said R' and R" optionally being substituted with a hydroxyl (—OH); sulfonic (—$SO_3$); sulfate (—$SO_4$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group, with $R_1$, $R_2$ and $R_3$ being, independently of each other, a linear or branched, saturated or unsaturated hydrocarbon-based radical containing 1 to 25 carbon atoms, with the proviso that the sum of the carbon atoms of $R_1+R_2$ does not exceed 26, and that the sum of the carbon atoms of $R_1+R_2$, $R_3$ does not exceed 27;

maleic anhydride;
itaconic acid;
vinyl alcohol of formula $CH_2$=CHOH;
vinyl acetate of formula $CH_2$=CH—$OCOCH_3$.

In addition to the monomers A mentioned above, which allow, alone or as a mixture, the production of a water-soluble unit having at least two reactive sites, it is possible to use, in combination with these monomers A, other monomers B that do not, by themselves, allow the production of a water-soluble unit having a reactive site.

Among the monomers B that may be mentioned, alone or as a mixture, are the monomers below, taken as they are or in the form of the organic or inorganic salts, for example, in the form of sodium, magnesium, ammonium or triethanolamine salts:

vinyl monomers of formula (IIb) below:

in which:
R is chosen from H, —$CH_3$, —$C_2H_5$ or —$C_3H_7$;
X is chosen from alkyl oxides of —OR' type in which R' is a linear or branched, saturated or unsaturated hydrocarbon-based radical containing from 1 to 8 carbons, optionally substituted with a sulfonic (—$SO_3$), sulfate (—$SO_4$), phosphate (—$PO_4H_2$); and/or quaternary amine (—$N^+R_1R_2R_3$) group, with $R_1$, $R_2$ and $R_3$ being, independently of each other, a linear or branched, saturated or unsaturated hydrocarbon-based radical containing 1 to 25 carbon atoms, with the proviso that the sum of the carbon atoms of $R_1+R_2+R_3$ does not exceed 27;
N-vinyllactams such as N-vinylpyrrolidone, N-vinylcaprolactam and N-butyrolactam;
vinyl ethers of formula $CH_2$=CHOR in which R is a linear or branched, saturated or unsaturated hydrocarbon-based radical containing from 1 to 25 carbons;
water-soluble derivatives of styrene, especially styrene sulfonate;
dimethyldiallylammonium chloride;
vinylacetamide.

Among the polycondensates and the natural polymers or modified natural polymers that may constitute all or part of the water-soluble units, mention may be made of:
  water-soluble polyurethanes having at least two reactive sites, especially bearing carboxylic acid functions;
  xanthan gum, especially the product sold under the names Keltrol T and Keltrol SF by Kelco; or Rhodigel SM and Rhodigel 200 from Rhodia;
  alginates (Kelcosol from Monsanto) and derivatives thereof such as propylene glycol alginate (Kelcoloid LVF from Kelco);
  cellulose derivatives and especially carboxymethylcellulose, hydroxypropylcellulose, hydroxyethylcellulose and quaternized hydroxyethylcellulose;

galactomannans and derivatives thereof, such as Konjac gum, guar gum, hydroxypropylguar, hydroxypropylguar modified with sodium methylcarboxylate groups, and hydroxypropyltrimethylammonium guar chloride.

Mention may also be made of polyethyleneimine.

The water-soluble units preferably have a molar mass of between 10 000 g/mol and 5 000 000 g/mol when they constitute the water-soluble backbone of a grafted polymer.

These water-soluble units preferably have a molar mass of between 5 000 g/mol and 100 000 g/mol when they constitute a block of a multiblock polymer.

As has been defined above, the water-soluble units bear at least two reactive sites, capable of reacting with at least one reactive site borne by the units with an LCST, so as to give a covalent bond.

This reactive site may be chosen especially from alcohol, isocyanate, primary, secondary or tertiary amine, carboxylic acid and halogen functions.

In particular, a reactive site of the carboxylic acid type will generally react with a reactive site of the alcohol or amine type; an isocyanate site will rather react with an alcohol site, and a halogen site will rather react with an alcohol or amine site.

The expression "units with an LCST" means units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, this heat-induced demixing temperature is observed; it is higher than the LCST, which is the minimum point of the curve. Below this temperature, the polymer is soluble in water; above this temperature, the polymer loses its solubility in water.

The expression "soluble in water" means that the units have a solubility at 20° C. of at least 1 g/l and preferably of at least 2 g/l.

The measurement of the LCST may be performed visually: the temperature at which the cloud point of the aqueous solution appears is determined; this cloud point is reflected by the opacification of the solution, or the loss of transparency.

In general, a transparent composition will have a maximum light transmittance value, irrespective of the wavelength of between 400 and 800 mm, through a sample 1 cm thick, of at least 80% and preferably of at least 90% (see EP-A-0 291 334).

The transmittance may be measured by placing a sample 1 cm thick in the light beam of a spectrophotometer working at the wavelengths of the light spectrum.

The units with an LCST used in the present invention consist of random copolymers of ethylene oxide and propylene oxide, which may be represented by the formula:

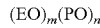

in which m is a number between 0 and 40 inclusive and n is a number between 15 and 60 inclusive.

Preferably, m is between 1 and 20 inclusive and n is between 20 and 50 inclusive.

Preferably, the molar mass of the units with an LCST is between 1 500 and 5 300 g/mol and especially between 2 000 and 4 000 g/mol.

It is observed that the random distribution of the EO and PO units results in the existence of a lower critical demixing temperature beyond which separation of macroscopic phases is observed.

This behavior is different from that of the block EO PO copolymers which micellize beyond a so-called micellization critical temperature (aggregation at the microscopic scale).

Needless to say, the units with an LCST also need to bear at least one reactive site capable of reacting with the reactive site borne by the water-soluble units, so as to form a covalent bond.

As previously, this reactive site may be chosen from alcohol, isocyanate, primary, secondary or tertiary amine, carboxylic acid and halogen functions.

When the final polymer consists of a water-soluble backbone and grafts with an LCST, the reactive sites are randomly distributed along the water-soluble backbone and those of the grafts are located on at least one of the ends of the chains with an LCST.

When the polymer is of multiblock type, the reactive sites are located at the ends of the water-soluble units and of the units with an LCST.

The units with an LCST may thus especially be in the form of random copolymers of ethylene oxide and propylene oxide, aminated, especially monoaminated, diaminated or triaminated.

Among the commercially available units with an LCST, mention may be made of the copolymers sold under the name Jeffamine by Huntsman, and especially Jeffamine XTJ-507 (M-2005), Jeffamine D-2000 and Jeffamine XTJ-509 (or T-3000).

The units with an LCST may also be in the form of polyalkylene glycols, random EO PO copolymers with OH ends, such as those sold under the names polyglycols P41 and B11 by Clariant.

Among the final polymers that may be used in the context of the invention, mention may be made in particular of:
polymers whose backbone consists of:
  a linear acrylic acid homopolymer;
  a linear copolymer of acrylic acid and of AMPS, and/or of acrylamide;
  a crosslinked homopolymer of polyacrylic acid;
  a natural derivative such as xanthan gum, alginates, carboxymethylcellulose or hydroxypropylguar modified with sodium methylcarboxylate groups;
or one of their organic or inorganic salts;
and bearing grafts with an LCST consisting of random copolymers of ethylene oxide and propylene oxide, aminated, especially monoaminated, diaminated or triaminated.

The proportion by mass of the units with an LCST in the final polymer is preferably between 5% and 70%, especially between 20% and 65% and particularly between 30% and 60% by weight relative to the final polymer.

Preferably, the heat-induced demixing temperature of LCST type of said units with an LCST is between 5° C. and 40° C. and preferably 10° C. and 35° C., for a concentration by mass in water of 1% by weight of said units with an LCST.

The polymers used in the context of the invention may be readily prepared by a person skilled in the art on the basis of his general knowledge.

In particular, when the final polymer is in the form of a grafted polymer especially containing a water-soluble backbone with grafted units with an LCST, it is possible to prepare it by grafting the chains with an LCST having at least one reactive end, especially aminated, on said water-soluble polymer forming the backbone, said polymer bearing at least 10% (on a molar basis) of carboxylic acid groups.

This reaction may be carried out in the presence of a carbodiimide such as dicyclohexylcarbodiimide or 1-(3-dimethylaminopropyl)-3-ethylcarbodiimide hydrochloride, in a solvent such as N-methylpyrrolidone or water.

To do this, inspiration may be taken from the preparation method described in the publication by Hourdet et al., Polymer, Vol. 38, No. 10, pp. 2535-2547, 1997.

This publication describes in particular the preparation of thermoassociative polymers comprising a water-soluble polyacrylic acid backbone onto which are grafted units with an LCST consisting of random copolymers of ethylene oxide and propylene oxide. However, the polymers described in this publication are not suitable in the present application because they have certain drawbacks, especially linked to the low molar mass of the grafts used; in particular, the graft called PPO has a molar mass of 600.

Indeed, when the molar mass of the grafts is too low, the gelling temperature of the final polymer does not completely correspond to the demixing temperature of the grafts with an LCST; a difference may exist between these two temperatures which may be up to 15 to 20° C. Prediction of the thermogelling properties with a view to industrial application then becomes complex.

Moreover, the quantity of units with an LCST to be incorporated into the polymer in order to have advantageous solution properties involves high grafting levels when the molar mass of the graft is not very high. This requires in particular the presence of a large proportion of reactive sites on the water-soluble backbone, hence a certain limitation in terms of structure and of synthesis.

Moreover, the combination of the grafts may become more difficult when they are smaller in size.

Another possibility for preparing grafted polymers consists in copolymerizing, for example, a macromonomer with an LCST (chain with an LCST described above with a vinyl end) and a water-soluble vinyl monomer such as acrylic acid or vinyl monomers having formula (IIa) or (IIb).

When the final polymer is in the form of a block polymer, it is possible to prepare it by coupling between water-soluble units and units with an LCST having complementary reactive sites at each end.

The polymers thus obtained are water-soluble and thermogellable.

They allow the production of thickened, or even gelled, aqueous compositions that especially have a viscosity which is constant or which increases when the temperature increases, and which moreover have good transparency.

In the context of the present invention, the expression "transparent solution or composition" has the standard definition given in the dictionary. Thus, a transparent composition readily allows light to pass through it and allows objects to be clearly distinguished through its thickness.

The transmittance may be measured by placing a sample 1 cm thick in the light beam of a spectrophotometer working in the wavelengths of the light spectrum.

In particular, the compositions thus prepared may have a maximum light transmittance value, irrespective of the wavelength of between 400 and 800 nm, through a sample 1 cm thick, of at least 80% and preferably of at least 85% (see EP-A-0 291 334).

The polymers according to the invention are preferably present in the aqueous compositions in an amount preferably of between 0.01% and 20% by weight, especially from 0.05% to 15% by weight and in particular from 0.1% to 10% by weight.

These compositions and the polymers they comprise find a most particular application in cosmetics and pharmaceuticals.

Said composition comprises, in addition to the polymer as defined above, an aqueous phase, which may comprise, in addition to water, a floral water such as cornflower water, a mineral water such as eau de Vittel, eau de Lucas or eau de La Roche Posay and/or a spring water.

The compositions according to the invention may contain an oily phase, for example, in the form of an oil-in-water emulsion, a water-in-oil emulsion or multiple emulsions such as water-in-oil-in-water emulsions.

It is possible to add to said aqueous composition the constituents usually used in the intended type of application. Needless to say, a person skilled in the art will take care to select these optional additional constituents, and/or the amount thereof, such that the advantageous properties of the composition according to the invention are not, or are not substantially, adversely affected by the envisaged addition.

Said aqueous composition may form all or part of a cosmetic or pharmaceutical composition which may thus moreover comprise a cosmetically or pharmaceutically acceptable medium, that is to say a medium that is compatible with use on keratin materials such as the skin, the nails, the hair, the eyelashes, the eyebrows, the mucous membranes and semi-mucous membranes, and any other area of body or facial skin.

Said composition thus finds a particular application as a cosmetic, make-up or care composition, which may be applied to the skin, the nails, the hair, the eyelashes, the eyebrows, mucous membranes and semi-mucous membranes, and any other area of body or facial skin.

The invention is illustrated in greater detail in the examples which follow.

EXAMPLE 1

In a 500 ml reactor equipped with a condenser, 3 grams of polyacrylic acid having an average molar mass of 450 000 g/mol (Aldrich) are dissolved in 220 ml of N-methylpyrrolidone, with stirring, at 60° C. for 12 hours.

4.181 grams of monoaminated random copolymer $(EO)_6(PO)_{39}$, having a molar mass of 2 600 g/mol, having a cloud point, at a concentration of 1% by weight in water, of 16° C. (Jeffamine M-2005 from Huntsman) are dissolved in 50 ml of N-methylpyrrolidone, with stirring, at 20° C., for 15 minutes. The solution obtained is added dropwise to the reaction medium containing polyacrylic acid, with vigorous stirring at 60° C.

2.158 grams of dicyclohexylcarbodiimide are dissolved in 30 ml of N-methylpyrrolidone, with stirring, at 20° C. for 15 minutes. The solution obtained is added dropwise to the reaction medium containing polyacrylic acid and the monoaminated random copolymer $(EO)_6(PO)_{39}$, with vigorous stirring at 60° C.

The final mixture is stirred for 12 hours at 60° C.

The mixtures is cooled to 20° C. and then it is placed in a refrigerator at 4° C. for 24 hours.

The dicyclohexylurea crystals formed are removed by filtration from the reaction medium.

The polymer is then neutralized with 19 g of 35% sodium hydroxide (4-fold excess relative to the number of moles of acrylic acid), which leads to its precipitation. After leaving to stand for 12 hours, the reaction medium is filtered so as to recover the precipitated polymer. The latter is dried under vacuum at 35° C. for 24 hours.

13.55 grams of solid are recovered, which are dissolved in 2 liters of deionized water. This solution is ultrafiltered using a Millipore ultrafiltration system containing a membrane whose cutoff threshold is set at 10 000 Daltons. The solution thus purified is freeze-dried so as to collect the polymer in solid form.

7.05 grams of sodium polyacrylate (450 000 g/mol) grafted with 3.9% (by mole) of monoaminated random copolymer $(EO)_6(PO)_{39}$ are obtained.

The proportion by mass of the units with an LCST in the final polymer is 51%.

The polymer thus obtained has a solubility in water, at 20° C., of at least 10 g/l.

EXAMPLE 2

In a manner similar to example 1, the following five polymers are prepared, in which the grafts are still a monoaminated random copolymer $(EO)_6 (PO)_{39}$:

| | Backbone | Proportion by mass of units with an LCST in the final polymer | Grafting level (mol %) |
|---|---|---|---|
| Example 2a | sodium polyacrylate (MW: 450 000) | 35% | 2% |
| Example 2b | sodium polyacrylate (MW: 750 000) | 58% | 5.2% |
| Example 2c | sodium polyacrylate (MW: 750 000) | 51% | 3.9% |
| Example 2d | sodium polyacrylate (MW: 450 000) | 59% | 5.3% |
| Example 2e | Carbomer (Carbopol 980 from Goodrich) in sodium salt form | 51% | 3.9% |

EXAMPLE 3

In a 1 liter reactor equipped with a condenser, 1.51 grams of polyacrylic acid having an average molar mass of 750 000 g/mol (Aldrich) are dissolved in 350 ml of deionized water, with stirring, at 20° C. for 12 hours. The pH of the reaction medium is then adjusted to 8 using a 1 M sodium hydroxide solution.

1.60 grams of monoaminated random copolymer $(EO)_6 (PO)_{39}$ (Jeffamine M-2005 from Huntsman) are dissolved in 100 ml of deionized water, with stirring, at 5° C. for 30 minutes. The solution obtained is added dropwise to the reaction medium, with vigorous stirring.

1.84 grams of 1-(3-dimethylaminopropyl)-3-ethyl carbodiimide hydrochloride are dissolved in 50 ml of deionized water, with stirring, at 20° C. for 15 minutes. The solution obtained is added, with vigorous stirring, dropwise, to the preceding reaction medium which is then heated at 60° C. for 6 hours.

The reaction medium is cooled to 20° C. and then concentrated and precipitated in acetone. The polymer, in solid form, is recovered by filtration and washed with an excess of acetone. The powder is ground and dried under vacuum at 35° C.

3.33 g of sodium polyacrylate (750 000 g/mol) grafted with 3.1% (by mole) of monoaminated random copolymer $(EO)_6 (PO)_{39}$ are obtained (yield 94%).

EXAMPLE 4

The polymers according to the invention are compared with the prior art polymers described in the publication by Hourdet et al., Polymer, vol. 38, no. 10, pp. 2535-2547, 1997.

Compounds tested:

| | Water-soluble backbone | Grafts (units with an LCST) | Proportion: units with an LCST in final polymer (by weight) | Grafting level (mol %) |
|---|---|---|---|---|
| Example 1 | sodium polyacrylate MW = 450 000 | monoaminated random $(EO)_6(PO)_{39}$; MW = 2 600 | 51% | 3.9% |
| Example 2a | sodium polyacrylate MW = 450 000 | monoaminated random $(EO)_6(PO)_{39}$; MW = 2 600 | 35% | 2% |
| Example 2d | sodium polyacrylate MW = 450 000 | monoaminated random $(EO)_6(PO)_{39}$; MW = 2 600 | 59% | 5.3% |
| Comparative 1 | sodium polyacrylate MW = 150 000 | monoaminated random $(EO)_1(PO)_9$; MW = 600 | 30% | 7% |
| Comparative 2 | sodium polyacrylate MW = 150 000 | monoaminated random $(EO)_1(PO)_9$; MW = 600 | 55% | 21% |

There is determined, for each of these compounds, at a given concentration in water, the difference between the gelling temperature Tgel of the aqueous polymer solution, and the demixing temperature Tdem of the grafts with an LCST alone.

$$\Delta T = T\text{gel} - T\text{dem}$$

The gelling temperature is determined using rheological curves measuring the viscosity as a function of the temperature, for the polymer solution on the one hand and for an aqueous solution of water-soluble backbone at a concentration identical to the concentration of water-soluble units in the polymer solution.

The gelling temperature is considered to have been reached when the difference between the viscosity of the polymer solution and the viscosity of the water-soluble backbone solution is greater than 5%. The method for measuring the viscosity is given in example 6.

The demixing temperature is determined visually, for a solution of grafts with an LCST alone, at a concentration identical to the concentration of grafts in the polymer solution.

The demixing temperature is considered to have been reached when the solution becomes white, that is to say is no longer transparent within the meaning of the present invention.

| Polymer | Concentration in water (% by weight) | Tgel | Tdem | ΔT |
|---|---|---|---|---|
| Example 1 | 2% | 28 | 23 | 5 |
| Example 1 | 5% | 23 | 19 | 4 |
| Example 2a | 2% | 33 | 27 | 6 |
| Example 2d | 5% | 22 | 19 | 3 |
| Comparative 1 | 2% | 65 | 49 | 16 |
| Comparative 1 | 5% | 63 | 46 | 17 |
| Comparative 2 | 2% | 30 | 47 | 13 |
| Comparative 2 | 5% | 53 | 41 | 12 |

Good agreement is therefore observed between the demixing temperature of the grafts with an LCST and the properties of the grafted polymer, for the polymers of the invention; that is not the case for the prior art polymers.

EXAMPLE 5

The polymers according to the invention are compared with the prior art polymers described in WO 95/24430.

The absorbance of aqueous solutions comprising these polymers is measured, by UV-visible spectroscopy, at a wavelength equal to 500 nm, at a temperature of 35° C. and of 40° C.

The transmittance is deduced therefrom according to the relationship: absorbance=−log transmittance.

The following results are obtained:

|  | Transmittance | |
| --- | --- | --- |
|  | at 35° C. | at 40° C. |
| Comparison 1 at 0.2% by weight in water | 76% | 63% |
| Comparison 2 at 0.2% by weight in water | 50% | 42% |
| Polymer of example 1 at 5% by weight in water | 89% | 88% |
| Polymer of example 2a at 2% by weight in water | 88% | 87% |

Comparison 1: block copolymer poly(N-isopropylacrylamide) and polyacrylic acid 24/76 (FIG. 1 of WO-95/24430).
Comparison 2: block copolymer poly(N-isopropylacrylamide) and polyacrylic acid 43/57 (FIG. 1 of WO-95/24430).

It is thus observed that the polymer according to the invention gives compositions that are markedly more transparent than those of the prior art.

EXAMPLE 6

A thermogellable aqueous gel is prepared, comprising:

| polymer of example 1 (dry matter) | 5 g |
| --- | --- |
| sodium chloride | 1.17 g |
| water | qs 100 g. |

This composition is prepared by simple introduction of the polymer into salted water with stirring for 2 hours at 20° C.

The viscosity of the composition is measured, at 20° C. and at 32° C., using a Haake RS150 rheometer equipped with a cone/plate geometry 3.5 cm/2° or 6 cm/2° and a temperature control system. The viscosity measurements are carried out in the flow mode by imposing a shear rate equal to 10 s$^{-1}$.

The following results are obtained:
viscosity at 20° C.: 0.015 Pa·s;
viscosity at 32° C.: 5 Pa·s.

The invention claimed is:

1. A cosmetic or pharmaceutical composition for use on keratin materials, said composition comprising an aqueous composition comprising a block polymer, said block polymer comprising water-soluble units alternating with one or more LCST units;
wherein said water-soluble units comprise at least one monomer A selected from the group consisting of (meth) acrylic acid, a (meth)acrylic acid organic salt, a (meth) acrylic acid inorganic salt, and mixtures thereof, said water-soluble units having a reactive site located at each end of the water-soluble units; and
wherein said one or more LCST units have a lower critical solution temperature and a molar mass of between 1,500 and 5,300 g/mol, wherein said LCST unit(s) comprise random copolymers of ethylene oxide and propylene oxide, said random copolymers having a reactive site located and each end of the random copolymer and having an ethylene oxide number of from 1 to 40 and a propylene oxide number of from 15 to 60, and salts thereof,
wherein the block polymer is formed by coupling the water-soluble units with the LCST units through reaction of the water-soluble unit reactive site with the LCST unit reactive site.

2. The composition as claimed in claim 1, wherein the water-soluble units present have a molar mass of between 10,000 g/mol and 5,000,000 g/mol.

3. The composition as claimed in claim 1, wherein the LCST units comprise random copolymers of ethylene oxide and propylene oxide of formula $(EO)_m(PO)_n$ in which m is a number of from 1 to 20 and n is a number of from 20 to 50.

4. The composition as claimed in claim 1, wherein the molar mass of the LCST units is between 2,000 and 4,000 g/mol.

5. The composition as claimed in claim 1, wherein the LCST units are aminated.

6. The composition as claimed in claim 1, wherein the LCST units are monoaminated, diaminated or triaminated.

7. The composition as claimed in claim 1, wherein the proportion by mass of the LCST units is between 5% and 70% by weight relative to the polymer.

8. The composition as claimed in claim 1, wherein the proportion by mass of the LCST units is between 20% and 65% by weight relative to the polymer.

9. The composition as claimed in claim 1, wherein the proportion by mass of the LCST units is between 30% and 60% by weight relative to the polymer.

10. The composition as claimed in claim 1, wherein the lower critical solution temperature is between 5° C. and 40° C. for a concentration by mass in water of 1% by weight of said LCST units.

11. The composition as claimed in claim 1, wherein the lower critical solution temperature is between 10° C. and 35° C. for a concentration by mass in water of 1% by weight of said LCST units.

12. The composition as claimed in claim 1, wherein the polymer has a solubility in water at 20° C. of at least 10 g/l.

13. The composition as claimed in claim 1, wherein the polymer has a solubility in water at 20° C. of at least 20 g/l.

14. The composition as claimed in claim 1, wherein the composition has a maximum light transmittance value between 400 and 800 nm, through a sample 1 cm thick, of at least 80%.

15. The composition as claimed in claim 1, wherein the composition has a maximum light transmittance value between 400 and 800 nm through a sample 1 cm thick of at least 85%.

16. The composition as claimed in claim 1, wherein the aqueous composition comprises an aqueous phase.

17. The composition as claimed in claim 1, wherein the at least one polymer is present in an amount of between 0.01% and 20% by weight of the aqueous composition.

18. The composition as claimed in claim 1, further comprising a cosmetically or pharmaceutically acceptable medium.

19. A transparent cosmetic composition comprising the composition of claim 1.

20. The composition as claimed in claim 1, wherein the aqueous composition further comprises an oily phase, yielding an emulsion.

* * * * *